(12) United States Patent
Drmanovic

(10) Patent No.: US 10,813,834 B2
(45) Date of Patent: Oct. 27, 2020

(54) DISINFECTING CAPPING DEVICE FOR SHARP MEDICAL OBJECTS

(71) Applicant: DRMA GROUP INTERNATIONAL LLC, Palm City, FL (US)

(72) Inventor: Zoran Drmanovic, Palm City, FL (US)

(73) Assignee: DRMA Group International LLC, Palm City, FL (US)

( * ) Notice: Subject to any disclaimer, the term of this patent is extended or adjusted under 35 U.S.C. 154(b) by 0 days.

(21) Appl. No.: 16/252,759

(22) Filed: Jan. 21, 2019

(65) Prior Publication Data

US 2019/0151201 A1 May 23, 2019

Related U.S. Application Data

(63) Continuation of application No. 15/450,084, filed on Mar. 6, 2017, now Pat. No. 10,182,968.

(51) Int. Cl.
*A61L 2/26* (2006.01)
*A61J 1/14* (2006.01)
*A61L 2/18* (2006.01)
*A61M 5/32* (2006.01)
*A61M 5/00* (2006.01)

(52) U.S. Cl.
CPC .............. *A61J 1/1443* (2013.01); *A61L 2/18* (2013.01); *A61L 2/26* (2013.01); *A61M 5/001* (2013.01); *A61M 5/3202* (2013.01); *A61L 2202/24* (2013.01); *A61M 2205/0205* (2013.01)

(58) Field of Classification Search
CPC . A61L 2/18; A61L 2/26; A61M 5/001; A61M 5/3202
See application file for complete search history.

(56) References Cited

U.S. PATENT DOCUMENTS

| | | |
|---|---|---|
| 2,400,722 A | 5/1946 | Swan |
| 4,340,052 A | 7/1982 | Dennehey et al. |
| 4,440,207 A | 4/1984 | Genatempo et al. |
| 5,053,003 A | 10/1991 | Dadson et al. |
| 5,242,425 A | 9/1993 | White et al. |
| 5,295,975 A | 3/1994 | Lockwood, Jr. |
| 5,324,264 A | 6/1994 | Whitaker |
| 5,429,612 A | 7/1995 | Berthier |
| 5,681,283 A | 10/1997 | Brownfield |
| 5,792,120 A | 8/1998 | Menyhay |
| 5,885,249 A | 3/1999 | Irisawa |
| 6,045,539 A | 4/2000 | Menyhay |
| 6,171,287 B1 | 1/2001 | Lynn et al. |
| 6,322,540 B1 | 11/2001 | Grabis et al. |

(Continued)

FOREIGN PATENT DOCUMENTS

| | | |
|---|---|---|
| EP | 0409180 A1 | 1/1991 |
| EP | 0520930 A1 | 12/1992 |

(Continued)

*Primary Examiner* — Timothy C Cleveland
(74) *Attorney, Agent, or Firm* — Dmitry Zuev, Esq.

(57) ABSTRACT

A disinfecting capping device for a sharp medical object, such as a medical needle, is provided. The device includes a container comprising a bottom, an open end opposite to the bottom, and a side disposed between the open end and the bottom of the container. The device further includes a first disinfecting member disposed on the internal surface of the side of the container between the open end and the bottom thereof so as to form a cavity for receiving the sharp medical object through the open end of the container.

16 Claims, 9 Drawing Sheets

(56) References Cited

U.S. PATENT DOCUMENTS

| | | |
|---|---|---|
| 6,391,003 B1 | 5/2002 | Lesch, Jr. |
| 6,409,706 B1 | 6/2002 | Loy |
| 6,547,764 B2 | 4/2003 | Larsen et al. |
| 6,582,408 B1 | 6/2003 | Buch-Rasmussen et al. |
| 6,908,460 B2 | 6/2005 | Distefano |
| 7,682,561 B2 | 3/2010 | Davis et al. |
| 7,815,611 B2 | 10/2010 | Giambattista et al. |
| 7,931,877 B2 | 4/2011 | Steffens et al. |
| 8,065,773 B2 | 11/2011 | Vaillancourt et al. |
| 8,069,523 B2 | 12/2011 | Vaillancourt et al. |
| 8,172,825 B2 | 5/2012 | Solomon et al. |
| 8,177,761 B2 | 5/2012 | Howlett et al. |
| 8,197,749 B2 | 6/2012 | Howlett et al. |
| 8,231,587 B2 | 7/2012 | Solomon et al. |
| 8,298,196 B1 | 10/2012 | Mansour |
| 8,328,767 B2 | 12/2012 | Solomon et al. |
| 8,336,151 B2 | 12/2012 | Kerr et al. |
| 8,336,152 B2 | 12/2012 | Vaillancourt et al. |
| 8,343,112 B2 | 1/2013 | Solomon et al. |
| 8,491,546 B2 | 7/2013 | Hoang et al. |
| 8,523,830 B2 | 9/2013 | Solomon et al. |
| 8,523,831 B2 | 9/2013 | Solomon et al. |
| 8,641,681 B2 | 2/2014 | Solomon et al. |
| 8,647,308 B2 | 2/2014 | Solomon et al. |
| 8,647,326 B2 | 2/2014 | Solomon et al. |
| 8,671,496 B2 | 3/2014 | Vaillancourt et al. |
| 8,696,820 B2 | 4/2014 | Vaillancourt et al. |
| 8,734,384 B2 | 5/2014 | Boyd et al. |
| 8,740,864 B2 | 6/2014 | Hoang et al. |
| 8,784,388 B2 | 7/2014 | Charles et al. |
| 8,961,475 B2 | 2/2015 | Solomon et al. |
| 8,999,073 B2 | 4/2015 | Rogers et al. |
| 9,039,989 B2 | 5/2015 | Liu et al. |
| 9,079,692 B2 | 7/2015 | Solomon et al. |
| 9,114,915 B2 | 8/2015 | Solomon et al. |
| 9,186,707 B2 | 11/2015 | Vaillancourt et al. |
| 9,192,449 B2 | 11/2015 | Kerr et al. |
| 9,259,284 B2 | 2/2016 | Rogers et al. |
| 9,283,367 B2 | 3/2016 | Hoang et al. |
| 9,283,368 B2 | 3/2016 | Hoang et al. |
| 9,283,369 B2 | 3/2016 | Ma et al. |
| 2008/0177250 A1 | 7/2008 | Howlett et al. |
| 2009/0137969 A1 | 5/2009 | Colantonio et al. |
| 2009/0307449 A1 | 12/2009 | Prahlad et al. |
| 2010/0272379 A1 | 10/2010 | Hu et al. |
| 2011/0054440 A1 | 3/2011 | Lewis |
| 2012/0302970 A1 | 11/2012 | Tennican |
| 2013/0171030 A1 | 7/2013 | Ferlic et al. |
| 2015/0360021 A1 | 12/2015 | Limdico et al. |
| 2017/0232121 A1 | 8/2017 | Chiu et al. |
| 2018/0055962 A1 | 3/2018 | Drmanovic |
| 2018/0064604 A1 | 3/2018 | Drmanovic |
| 2018/0071508 A1 | 3/2018 | Drmanovic |
| 2018/0085568 A1 | 3/2018 | Drmanovic |

FOREIGN PATENT DOCUMENTS

| | | |
|---|---|---|
| EP | 0832661 A2 | 4/1998 |
| EP | 1336419 A1 | 8/2003 |
| WO | 2015120336 A1 | 8/2015 |

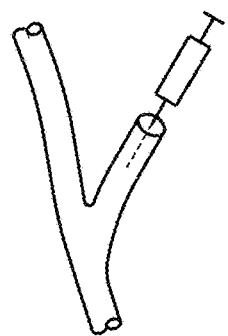
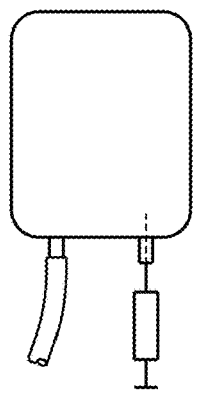
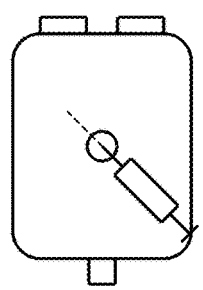
Fig. 1A    Fig. 1B    Fig. 1C
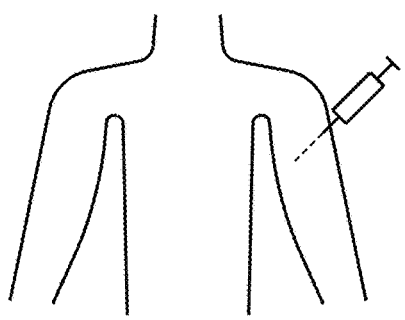
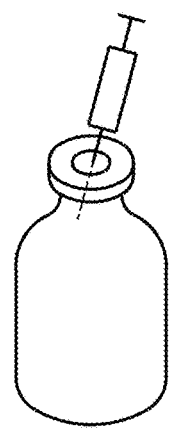
Fig. 1D    Fig. 1E
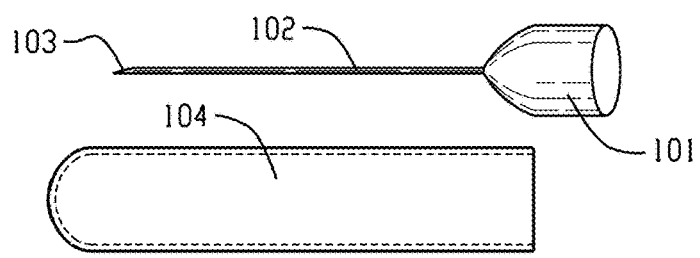
Fig. 2A
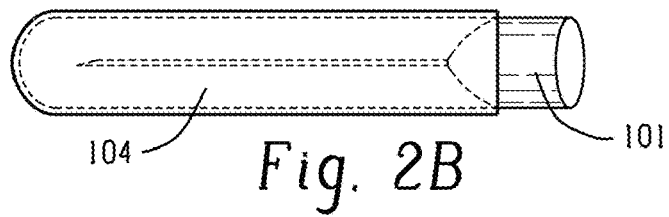
Fig. 2B

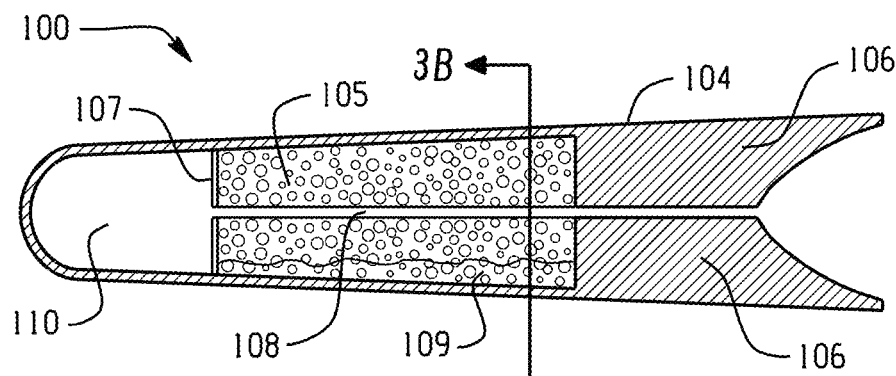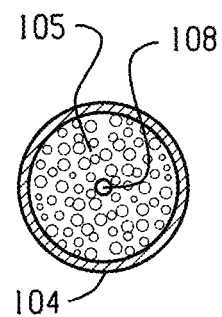
Fig. 3A
Fig. 3B
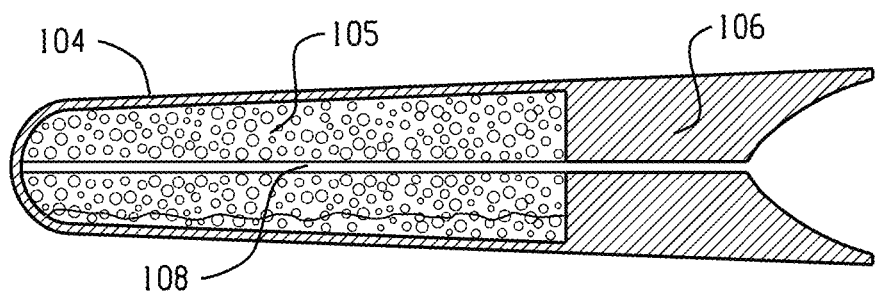
Fig. 3C
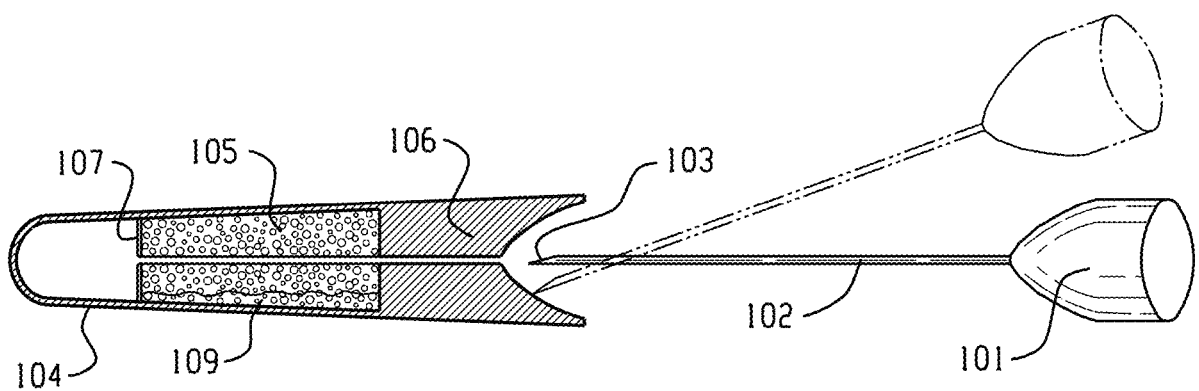
Fig. 4

DISINFECTING CAPPING DEVICE FOR SHARP MEDICAL OBJECTS

CROSS-REFERENCE TO RELATED APPLICATIONS

This application is a continuation of U.S. patent application Ser. No. 15/450,084 filed on Mar. 6, 2017 in the United States Patent and Trademark Office, the content of which is incorporated herein in its entirety by reference.

BACKGROUND

The present invention generally relates to a device having disinfecting properties, and more specifically, to a capping device for disinfecting needles, catheters, spikes and other sharp medical objects.

Infected (contaminated) needles, catheters, and spikes, are the major risk factor for the development of bloodstream infections. They are usually used to inject or withdraw medications, fluid, and blood products by penetrating different types of membranes or, in some cases, a patient's skin.

Scrubbing of these membranes or a patient's skin with alcohol for 10-60 seconds is recommended before each use, but this procedure is often omitted by medical professionals. This leads to potential contamination of needles, catheters and spikes. When these contaminated objects are used to penetrate another clean membrane, they may cause bloodstream infection. Needles, catheters, and spikes can also get contaminated when they are left open without a protective cover on a contaminated surface. Studies have shown better results in reducing infection with different types of alcohol impregnated protectors.

Needles and other sharp objects arrive at hospitals in sterile, sealed packages. However, once a medical professional opens the package, the needle is exposed to a potentially contaminated environment. Usually, a needle is attached to a syringe, when it is used to draw medication from a vial or an IV bag, or when it is used to inject medication. When the needle or any other sharp object is separated from the plastic cover it may be placed on a potentially contaminated surface.

While it is not recommended to use the same needle or some other sharp medical object more than once, there are circumstances where this practice is necessary and justified. Sometimes during a surgery, a medical provider has to repeatedly draw the medication from the same vial or the same IV bag within a few hours. Providers usually use the same needle attached to the same syringe labeled for that medication. While using the needle to draw medication from the vial, a plastic cover is usually placed on the same surface which might be contaminated. The plastic cover is then placed at the top of the needle, and if this cover is contaminated, it will contaminate the needle too. Needles, spikes, and other sharp medical objects can also get contaminated when they are used to penetrate the contaminated rubber membrane of the vial or an IV bag injection port, if the sharp medical objects are not wiped with alcohol before penetration.

An example of using the same needle and the same syringe for multiple penetrations of vials and IV bags is getting an additional volume of muscle relaxant from the same vial while using the same needle and the same syringe already labeled with the medication. Another example is when a provider in a heart room penetrates an IV bag with phenylephrine, epinephrine or norepinephrine multiple times with the same needle attached to the same syringe. This is a common and accepted practice. Occasionally, under pressure and stress, providers may utilize the same needle or some other sharp object even in cases where this should not be done.

Multiple uses of the same needles and poor aseptic techniques are prevalent in the intravenous drug abuser population as well as patients in underdeveloped countries. Although the goal should remain to provide sterile, single use needles and syringes, the capping device would be able to help a non-compliant group of this population reduce the number of HIV, Hepatitis C and B, and bacterial endocarditis cases. This is especially the case when this device would be used together with the disinfecting luer connecting device. The device would also help the population of the underdeveloped countries where medical supplies are difficult to find.

Thus, there remains a need for a convenient and reliable disinfecting capping device that would allow medical professionals to carry out multiple drawings, injections, or penetrations without causing contamination and blood stream infection.

SUMMARY

In an embodiment, a disinfecting capping device for a sharp medical object, such as a medical needle, is provided. The device includes a container comprising a bottom, an open end opposite to the bottom, and a side disposed between the open end and the bottom of the container. The device further includes a first disinfecting member disposed on the internal surface of the side of the container between the open end and the bottom thereof so as to form a cavity for receiving the sharp medical object through the open end of the container.

The disinfecting capping device may further include a membrane disposed inside the container between the open end and the bottom thereof in a direction substantially perpendicular to an internal surface of the side of the container so as to form a first chamber. The membrane may have an opening, and the cavity of the container may be in communication with the first chamber thereof through the membrane opening.

The open end of the container may include a funnel having a proximal (outer) end and a distal (inner) end so as to guide the sharp medical object through the distal end inside the cavity. A diameter of the cavity may be equal to or less than an external diameter of the sharp medical object.

The disinfecting member may be disposed between the membrane and the distal end of the funnel. The disinfecting member may be permanently affixed to the internal surface of the side of the container.

The disinfecting member may be impregnated with a disinfecting agent. The disinfecting agent may be an antibacterial agent, an anti-viral agent, or a combination thereof.

The disinfecting capping device may further include an external member attached to the bottom of the container, and a second disinfecting member attached to the external member.

The cap may be detachable from the external member. The external member may be permanently affixed to the bottom of the container.

The disinfecting capping device may further include a cap covering the second disinfecting pad, which may form a seal with the external member of the container.

The cap may be detachable from the external member, and the external member may be permanently affixed to the bottom of the container. The second disinfecting pad is attached to an internal surface of the external member.

Yet another embodiment provides a method for disinfecting a sharp medical object. According to the method, a disinfecting capping device for a sharp medical object is provided. The device includes a container comprising a bottom, an open end opposite to the bottom, and a side disposed between the open end and the bottom of the container. The device further includes a first disinfecting member disposed on the internal surface of the side of the container between the open end and the bottom thereof so as to form a cavity for receiving the sharp medical object through the open end of the container. The method further includes inserting the sharp medical object through the open end into the container to bring an external surface of the sharp medical object in contact with the disinfecting member, and disinfecting the external surface of the sharp medical object.

The disinfecting capping device may further include a membrane disposed inside the container between the open end and the bottom thereof in a direction substantially perpendicular to an internal surface of the side of the container so as to form a first chamber.

The membrane may have an opening, and the cavity of the container may be in communication with the first chamber thereof through the membrane opening.

The inserting the sharp medical object through the open end into the container may be followed by penetrating the membrane opening with a tip of the sharp medical object.

The method may further include removing the disinfected sharp medical object from the disinfecting capping device, and reusing the sharp medical object.

BRIEF DESCRIPTION OF THE DRAWINGS

The above and other aspects and features of the present disclosure will become more apparent by describing in detail exemplary embodiments thereof with reference to the attached drawings, in which:

FIG. 1A shows a needle penetrating a rubber membrane of a typical intravenous tubing;

FIG. 1B shows a needle penetrating an injection port on a typical intravenous bag;

FIG. 1C shows a needle penetrating a "belly button" membrane of a different type of the intravenous bag;

FIG. 1D shows a needle penetrating a patient's skin and muscle;

FIG. 1E shows a needle penetrating a rubber membrane located on a medication vial;

FIG. 2A shows a typical injection needle outside its protective plastic cover;

FIG. 2B shows a typical injection needle inside its protective plastic cover;

FIG. 3A is a longitudinal cross-sectional view of the device, according to an embodiment;

FIG. 3B is a transverse cross-sectional view of the device, according to an embodiment, at the level of the disinfecting pads;

FIG. 3C is a longitudinal cross-sectional view of the device, according to another embodiment;

FIG. 4 shows the same device according to an embodiment and a typical medical needle coming into contact with the device;

FIG. 9 shows a longitudinal cross-sectional view of the disinfecting apparatus, according to an embodiment, with the protective plastic cap on;

DETAILED DESCRIPTION

Figure 5:
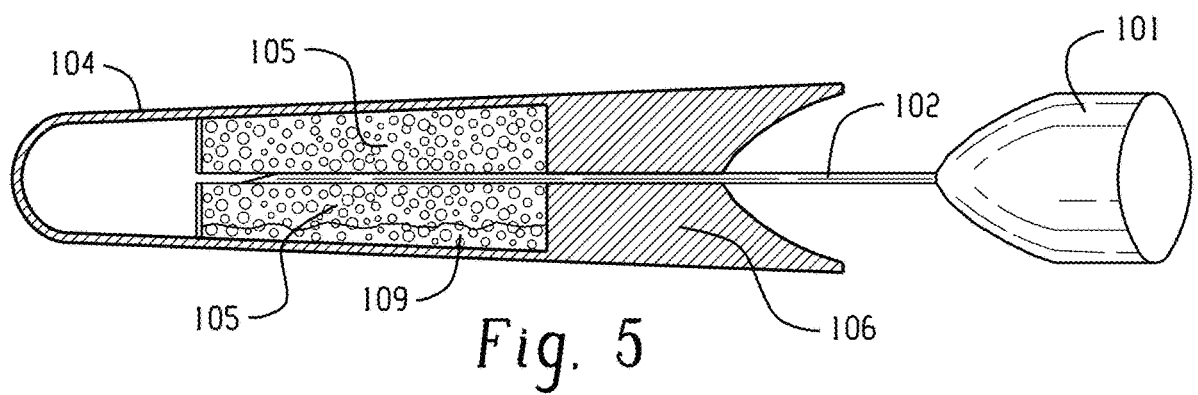
FIG. 5 shows a needle partially entering the device, according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below by referring to the figures to explain aspects of the present disclosure. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third, etc., may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross-section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"Substantially" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "substantially" can mean within one or more standard deviations, or within ±30%, 20%, 10%, 5% of the stated value.

In an embodiment, a disinfecting capping device for a sharp medical object, such as a medical needle, is provided. The device includes a container comprising a bottom, an open end opposite to the bottom, and a side disposed between the open end and the bottom of the container. The device further includes a first disinfecting member disposed on the internal surface of the side of the container between the open end and the bottom thereof so as to form a cavity for receiving the sharp medical object through the open end of the container.

The disinfecting capping device may further include a membrane disposed inside the container between the open end and the bottom thereof in a direction substantially perpendicular to an internal surface of the side of the container so as to form a first chamber. The membrane may have an opening, and the cavity of the container may be in communication with the first chamber thereof through the membrane opening.

The disinfecting capping device may further include an external member attached to the bottom of the container, and a second disinfecting member attached to the external member.

In yet another embodiment, a method for disinfecting a sharp medical object is provided. According to the method, a capping device for a sharp medical object is provided. The device includes a container comprising a bottom, an open end opposite to the bottom, and a side disposed between the open end and the bottom of the container. The device further includes a first disinfecting member disposed on the internal surface of the side of the container between the open end and the bottom thereof so as to form a cavity for receiving the sharp medical object through the open end of the container. The method further includes inserting the sharp medical object through the open end into the container to bring an external surface of the sharp medical object in contact with the disinfecting member, and disinfecting the external surface of the sharp medical object.

The disinfecting capping device may further include a membrane disposed inside the container between the open end and the bottom thereof in a direction substantially perpendicular to an internal surface of the side of the container so as to form a first chamber. The membrane may have an opening, and the cavity of the container may be in communication with the first chamber thereof through the membrane opening.

The inserting the sharp medical object through the open end into the container may be followed by penetrating the membrane opening with a tip of the sharp medical object.

The method may further include removing the disinfected sharp medical object from the disinfecting capping device, and reusing the sharp medical object.

FIGS. 1A to 1E illustrate several of the many situations in which a sharp object such as a needle, a spike, or a catheter penetrates different injection membranes or a patient's body. FIG. 1A shows a medical needle penetrating the rubber membrane of a typical intravenous or intra-arterial tubing. FIG. 1B shows a needle going through the injection port of a typical IV bag. FIG. 1C shows a needle penetrating a so-called "belly button" membrane of a different type of an IV bag. FIG. 1D shows a needle used to inject medications into a patient's skin, muscle, or vein. FIG. 1E shows a needle penetrating a rubber membrane located on a typical medication vial in order to draw the medication into a syringe.

FIG. 2A shows a typical needle outside of its protective plastic cover 104. The needle has a hub 101, a shaft 102, and a bevel 103. FIG. 2B shows the same needle located inside its protective cover. The needle and the protective cover use a slip lock mechanism to connect to each other. The design of a common needle and its cover are well-known and will not be described in details here.

FIG. 3A shows the disinfecting device 100 according to an embodiment without a needle inside. The device can be made from the same material as the plastic protective cover 104 or from a different material. The selected material should provide a good fluid barrier to prevent loss of the disinfecting agent. The additional elements are a funnel 106, a disinfecting pad 105, a membrane 107 and a disinfecting agent 109. The funnel 106 can be made of some rigid material such as plastic and has two major functions. The first function is to allow slip lock engagement between the cover 104 and the needle. The second and perhaps more important function is to guide the needle bevel 103 through the proximal (outer) end of the funnel into the narrow lumen of the funnel. For very sharp needles, it is important that the narrow lumen of the funnel 106 matches the size of the needle precisely to assure that the needle goes straight through a cavity 108 created by the disinfecting pad 105. If the narrow lumen of the funnel 106 is too wide, the needle would be loose inside the narrow part and could enter the cavity 108 of the disinfecting pad 105 under different angles. This may cause the needle to puncture the pad 105 instead of going through the cavity 108. Although puncturing the pad would still disinfect the needle, it may also create an opportunity for a small piece of the disinfecting pad 105 to be cut by the tip of the needle and caught inside the lumen of the needle, obstructing it. A material used for the disinfecting pad 105 should be carefully chosen. Ideally, the material should have excellent absorbing ability to effectively disinfect the sharp medical object. On the other hand, the material should have good mechanical resistance to prevent its penetration by the needle. When the medical object is not sharp enough to be able to penetrate the disinfecting pad (such as a spike of a blood transfusion tubing discussed below), the internal diameter of the cavity 108 can be less than the external diameter of the medical spike. In the case of the latter objects, the disinfecting pad may not even form a lumen, but instead may have, for example, two perpendicular splits that would accept the medical object inside the disinfecting apparatus (the diameter of the lumen is about 0) as the portions of the pad comprising the splits are compressed by the medical object such as a medical spike. The membrane 107 provides a fluid barrier, keeps the disinfecting agent 109 inside the disinfecting pad 105, and thus, prevents drying of the disinfecting pad 105. The membrane 107 also prevents the disinfecting agent 109 from moving into the empty chamber 110 and potentially entering the needle's lumen via the bevel 103. In addition, some disinfecting agents may enter the lumen of the needle and interfere with the medications present there. The device, according to an embodiment, should come in a sterile, sealed package.

FIG. 3B shows a transverse cross-sectional cut of the device at the level of the disinfecting pad 105. An outer rim represents the plastic cover 104. In the middle of the disinfecting pad 105 is the cavity 108 which preferably corresponds in shape and size to the shape and size of the needle's shaft 102 (FIG. 2A). The disinfecting pad 105 lines the interior of the cover 104 and is affixed to the surface of the cavity. In an embodiment, the disinfecting pad 105 does not completely fill out the entire plastic cover 104. It leaves an empty space—the cavity 108 which matches the shape and size of the needle's shaft 102. This compatibility guarantees that the disinfecting pad 105 comes into close contact with the needle's shaft 102. The disinfecting pad 105 must have great absorption capacity. Movement of the device 100 also causes the disinfecting agent to migrate inside the device. The disinfecting pad 105 can be made from any suitable material having good absorbing ability, for example, a sponge. The disinfecting agent may include an antibacterial agent, an antiviral agent, or a combination thereof. The amount of the disinfecting agent is usually small and the good absorbing ability of the disinfecting pad 105 should be sufficient to absorb all of the disinfecting agent. The disinfecting pad 105 is soaked with a disinfecting agent such as povidone iodine, alcohol, chlorhexidine, etc., or any combination of the disinfecting agents that provides antiseptic, antibacterial, or antiviral properties. The disinfecting pad 105 can be made of a non-woven material such as polyester, silicone, cotton, polyurethane, or any other absorbent material known in the art. The amount of the absorbent material may vary.

FIG. 3C shows another embodiment of the disinfecting device, wherein the membrane 107 is absent, and wherein the cavity 108 created by the disinfecting pad 105 extends essentially all the inner surface of the way to the bottom of the device.

FIG. 4 shows the device 100 which is ready to accept the needle. The bevel 103 of the needle touches the funnel 106 which has a rigid but curved surface to guide the needle into the narrow lumen of the funnel 106 and further into the cavity 108 created by the pad 105. The length of the narrow lumen of the funnel 105 can vary but it has to be sufficiently long to keep the needle straight so that it enters precisely into the cavity 108 and does not puncture the disinfecting pad 105. A small amount of the disinfecting agent 109 is shown inside the disinfecting pad 105. The disinfecting agent 109 falls down by gravity, but frequent movements of the device to cover and uncover the needle or to draw or inject the medication would cause the disinfecting agent 109 to soak the entire pad. Since the needle is frequently attached to a syringe, the medical provider would move them together.

FIG. 5 shows an important, distal part of the needle contacting the disinfecting pad 105. Since only the distal half of the needle is designed to penetrate the membrane and enter a tubing, a bag, a vial, or a patient's body, the entire needle shaft does not need to enter inside the cavity 108. Accordingly, in an embodiment, placing a small disinfecting pad 105 in proximity to the funnel 106 may be sufficient to disinfect the distal part of the needle. Although longer disinfecting pads may be useful to absorb larger amounts of the disinfecting agent, they create an increased risk that the needle can puncture and penetrate the disinfecting pad upon moving inside the cavity 108. When this happens, a small piece of the absorbent material may get caught inside the needle shaft. The area close to the narrow lumen of the funnel 106 is the location where the needle bevel is forced to go straight into the cavity 108. However, the further the distal part of the needle moves away from the funnel 106 and into the cavity 108, it is more likely that the needle bevel can deviate from its horizontal path and move towards the periphery of the cavity 108 where it may penetrate the disinfecting pad 105.

The disinfecting pads 105 may be made of a non-woven material or a sponge including polyester, silicone, cotton, polyurethane, or any other suitable material. Preference should be given to a natural (non-synthetic) material and disinfectant which is not harmful to the human body even when a trace of the disinfectant enters the patient's circulation. The amount of the material for the disinfecting pad 105 may vary but the material needs to have good absorbing ability. The pad may be soaked with any disinfecting agent, that is known to possess antiseptic, antibacterial, or antiviral properties, for example, povidone iodine, alcohol, chlorhexidine, or any combination thereof. The disinfecting pad should also be sufficiently elastic so that it can bend out of the way and easily return to its original shape upon introduction of the needle.

Figure 6:
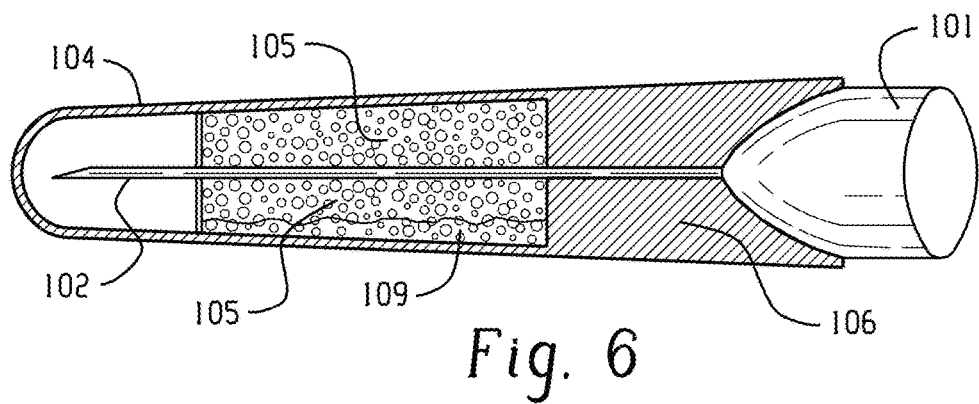
FIG. 6 shows the entire needle inside the disinfecting device, according to an embodiment.

FIG. 6 shows the entire needle inside the device 100. Only a small part of the hub 101 is located outside the protective cover 104, and this part of the hub serves to attach the hub to a syringe. The needle and the device 100 can be connected by the same slip lock mechanism as in an embodiment where the needle is connected to a regular plastic cover without any disinfecting pad inside. Alternative ways of connecting the device with the needle may also be used, for example, by using an original slip lock mechanism on the regular cover and placing the funnel 106 somewhat distally. In the latter case, the funnel 106 would not be responsible for attaching to the needle, but just for guiding the needle into the narrow part of the funnel 106.

Figure 7A:
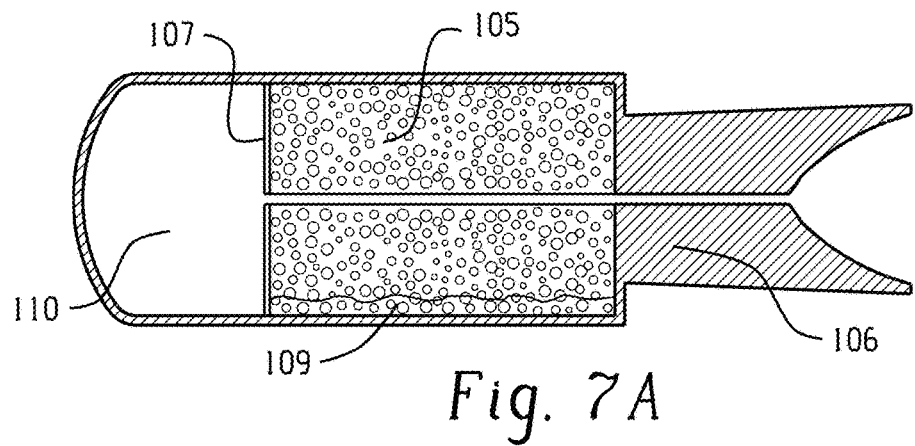
FIG. 7A shows a variation of the device, according to another embodiment.

FIG. 7A illustrates another embodiment of the device where the diameter of the funnel 106 is the same in order to receive the hub 101 of the most common, regular needles, while the diameter of the rest of the device is wider in order to allow more space to accommodate a bigger disinfecting pad 105 which may absorb a larger volume of the disinfecting agent 109. It is understood that the membrane 107 is also larger to prevent drying of the pad and leakage of the agent 109 into the empty chamber 110 which may then migrate toward the bevel 103. The larger diameter of the cover 104 minimizes chances of the disinfecting agent to enter the bevel 103 even if it crosses from the disinfecting pad 105 into the empty chamber 110 because the larger empty chamber 110 will permit the disinfecting agent to pool on its inner surface at a greater distance from the bevel 103.

Figure 7B:
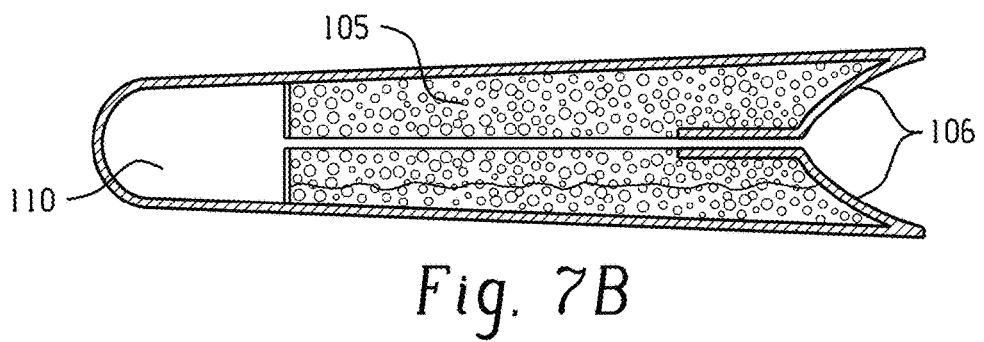
FIG. 7B shows another variation of the device, according to an embodiment.

FIG. 7B shows another modified version of the device. In this version the funnel 106 is not solid but hollow, thereby allowing an additional space for the disinfecting pad 105. The funnel 106 is attached to the cover 104 (or may be integral to the cover 104) only at its wider portion where the plastic cover 104, the funnel 106, and the needle hub 101 meet.

Figure 8A:
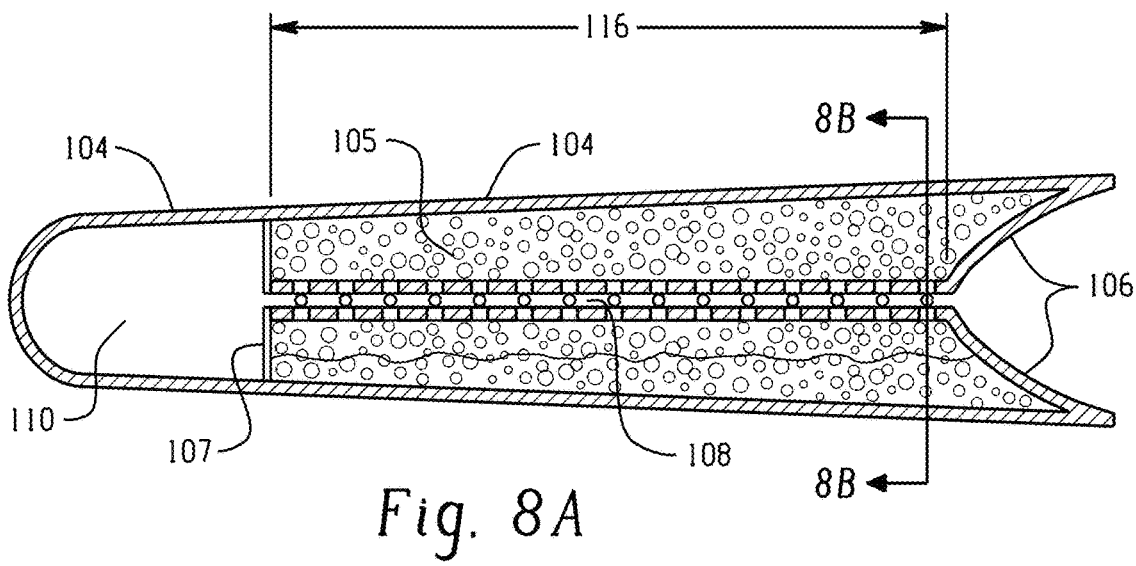
FIG. 8A shows a longitudinal cross-sectional view of the disinfecting apparatus having a fenestrated central lumen, according to an embodiment.

FIG. 8A shows a yet another modified version of the disinfecting device, according to an embodiment. This device has a central lumen 116 located inside the cavity 108, which is designed to guide the needle straight inside the cavity 108 without puncturing or perforating the disinfecting pad 105. To protect the disinfecting pad 105, it is important that the central lumen 116 be fabricated from a material having good mechanical resistance, for example, a hard polymer material. The walls of the central lumen 116 have a number of fenestrations (openings) which would allow the disinfecting agent to readily pass from the disinfecting pad through the fenestrations onto the surface of the needle. The small size of the fenestrations will also prevent the tip of the needle from puncturing the disinfecting pad 105. The fenestrations may be round, oval, square, rectangular, or may have any other desired shape. The internal diameter of the central lumen 116 should match the external diameter of the needle to provide optimal disinfection of the needle. In this embodiment, of the disinfecting device, the protecting cover 104 should be elastic enough to allow the provider to gently apply pressure on the protective cover 104 and the disinfecting pad 105 in order to release the disinfecting agent. Upon release, the disinfecting agent would pass through the fenestrations of the central lumen 116 onto the surface of the needle to disinfect the needle.

Figure 8B:
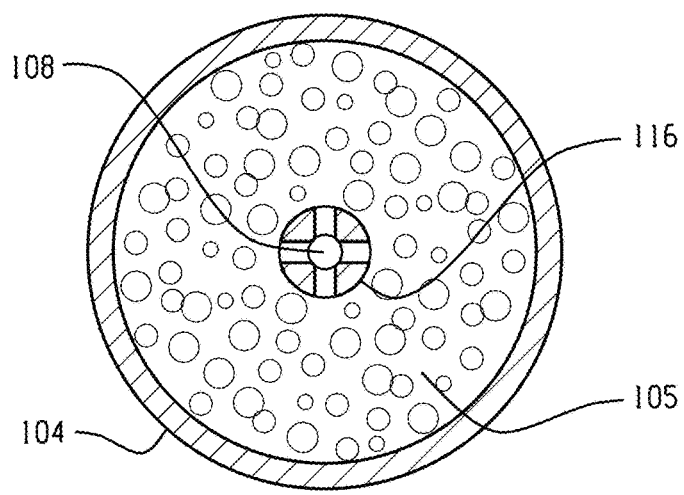
FIG. 8B shows a transverse cross-sectional view of the fenestrated central lumen of the disinfecting apparatus, according to an embodiment.
Figure 8C:
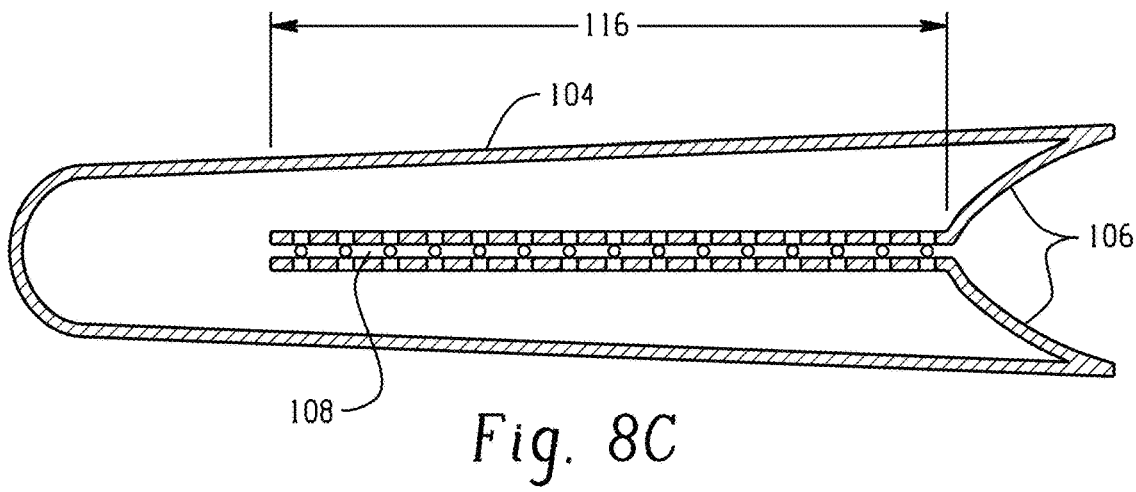
FIG. 8C shows a longitudinal cross-sectional view of the disinfecting apparatus having a fenestrated central lumen, according to an embodiment.
Figure 8D:
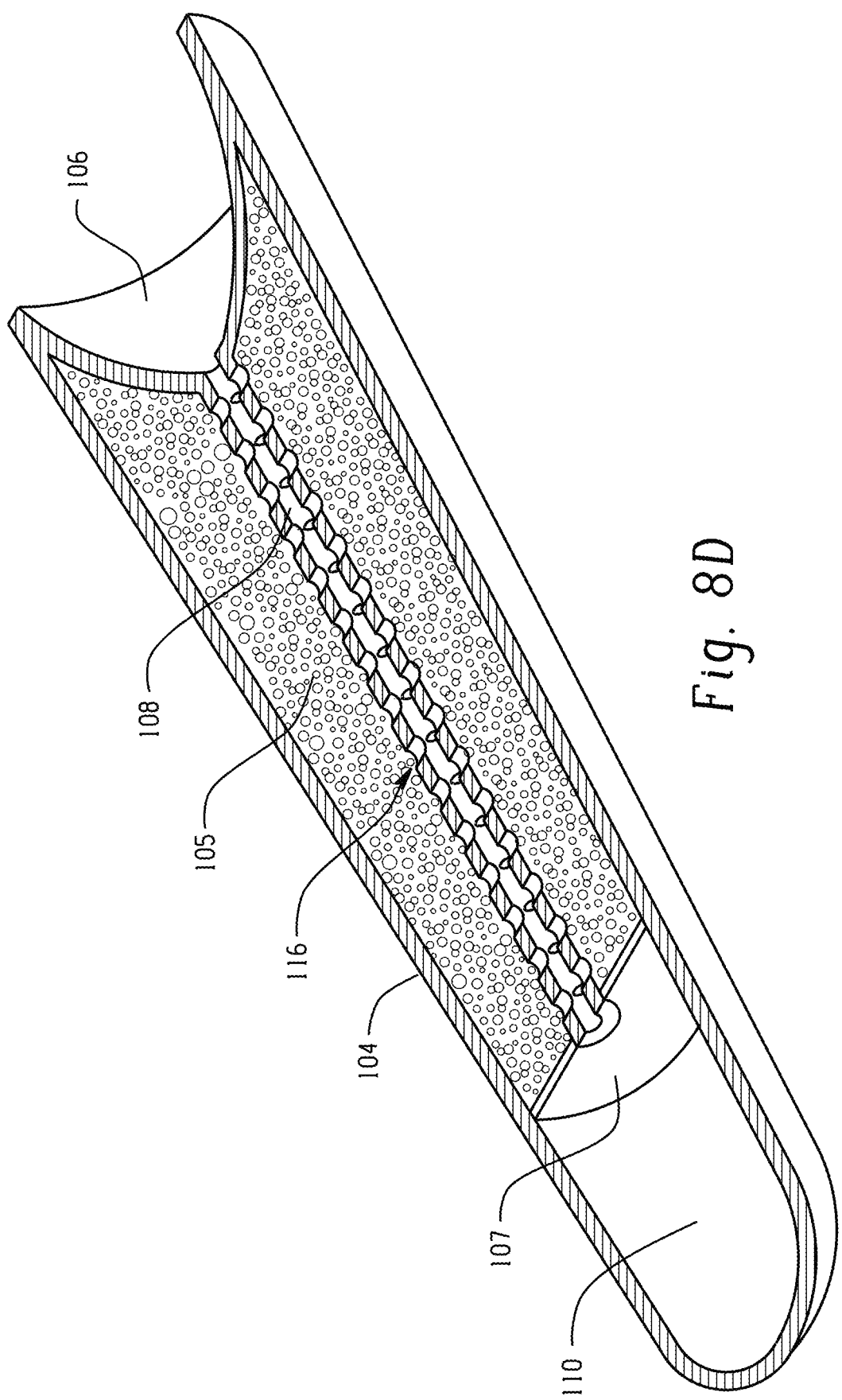
FIG. 8D shows a frontal cross-sectional perspective view of the disinfecting apparatus having a fenestrated central lumen, according to an embodiment.

FIG. 8B is a transverse cross-sectional representation of the disinfecting device shown in FIG. 8A, which has a side view of the cavity 108 containing the fenestrated central lumen 116. FIG. 8C is a schematic view of the disinfecting device according to an embodiment which only shows the fenestrated central lumen 116 located inside the cavity 108. FIG. 8D shows a frontal cross-sectional perspective view of the disinfecting device showing a fenestrated central lumen 116 bisected through its frontal plan.

Figure 9:
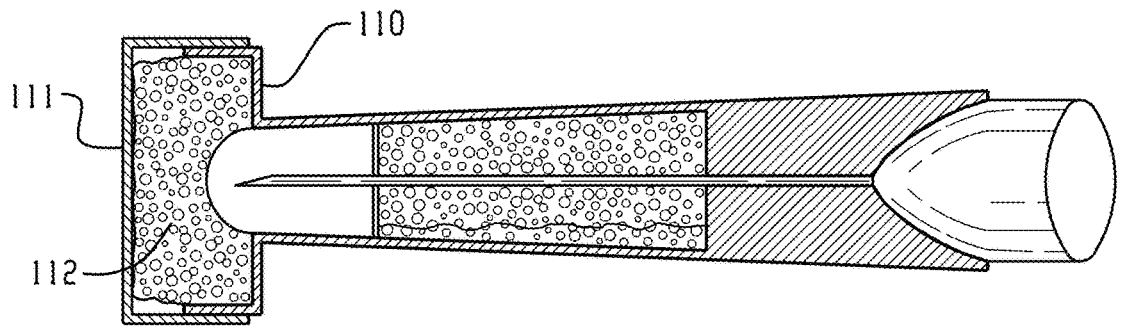

FIG. 9 shows another embodiment of the disinfecting apparatus, wherein the apparatus has an additional disinfecting chamber. According to this embodiment, the apparatus includes a base 110 attached to the distal part (bottom) of the cover 104, which holds an additional disinfecting pad 112. The additional disinfecting pad 112 containing the disinfecting agent is attached to the base 110. To prevent drying of the disinfecting pad 112 or leakage of the disinfecting agent, the apparatus is covered with a cap 111. While the base 110 and the cap 111 of the disinfecting apparatus are shown to be round, their shape and size may vary as desired. The disinfecting pad 112, like the main disinfecting pad 105, can be made from a well-absorbing material and is soaked with a disinfecting agent.

Figure 10:
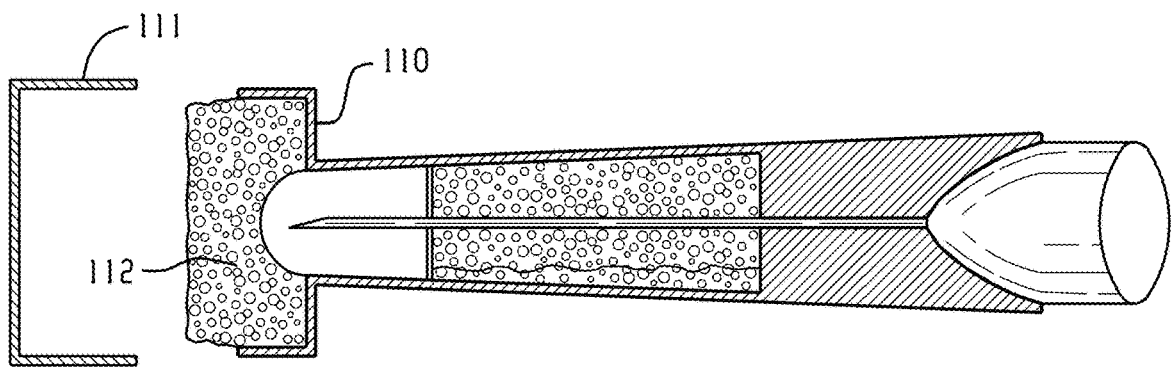
FIG. 10 shows a longitudinal cross-sectional view of the disinfecting apparatus, according to an embodiment, with the protective plastic cap removed.

FIG. 10 shows an additional disinfecting apparatus according to an embodiment, which has a cap 111 removed and the disinfecting pad 112 exposed.

Figure 11:
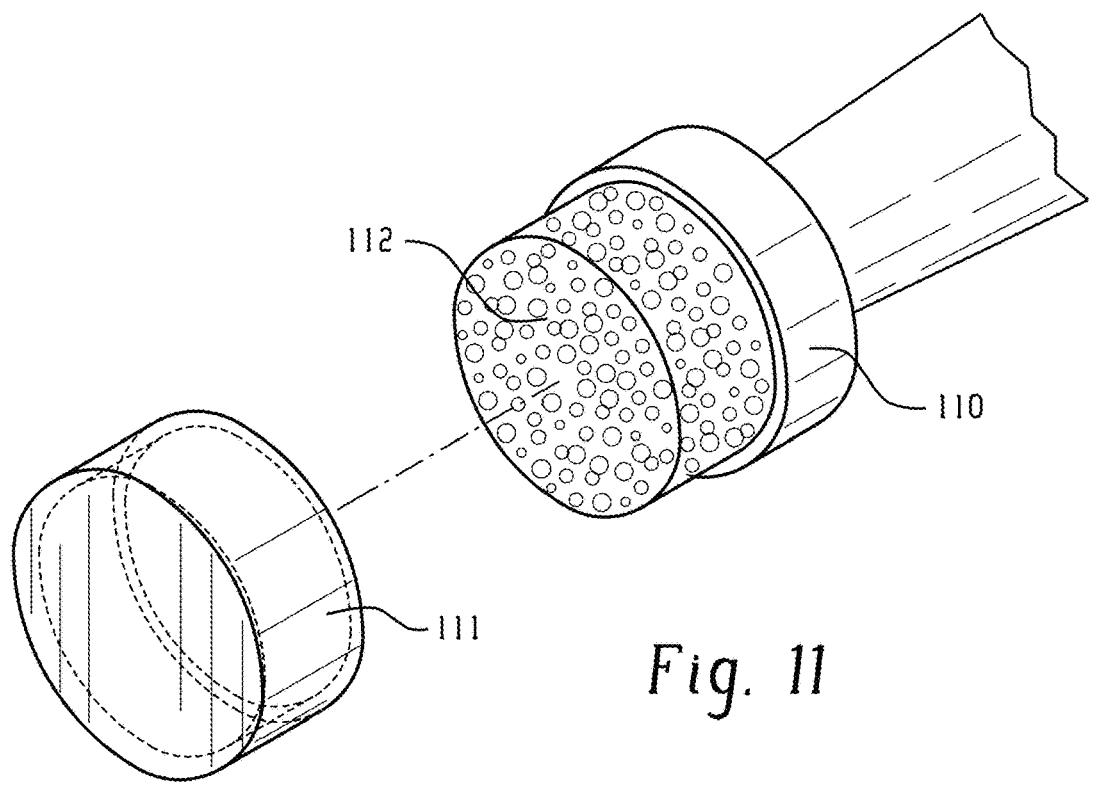
FIG. 11 shows a perspective view of an additional disinfecting pad of the disinfecting apparatus, according to an embodiment.

FIG. 11 shows a perspective view of the device 100 according to an embodiment. When the cap 111 is removed, the disinfecting pad 112 may be soaked with a disinfecting agent. Before the needle penetrates any rubber membrane, vial, IV tubing, or patient's skin, those surfaces need to be wiped with an alcohol swab. Since, in some cases, an alcohol swab might not be available, the presence of the additional disinfecting chamber on the device assures that the surfaces will be clean. Presence of the additional disinfecting chamber at the top of the cover would also remind the provider to clean the surface before it penetrates with the needle. This may be especially important in the intravenous drug abuser population where multiple uses of the same needle, sharing of needles, and absence of alcohol swabs present serious health concerns and lead to the spread of blood borne infections. Another group which might benefit from this device and its additional disinfecting chamber are the patients in underdeveloped countries, where lack of medical supplies is prevalent, and where aseptic techniques are not followed strictly.

Figure 12:
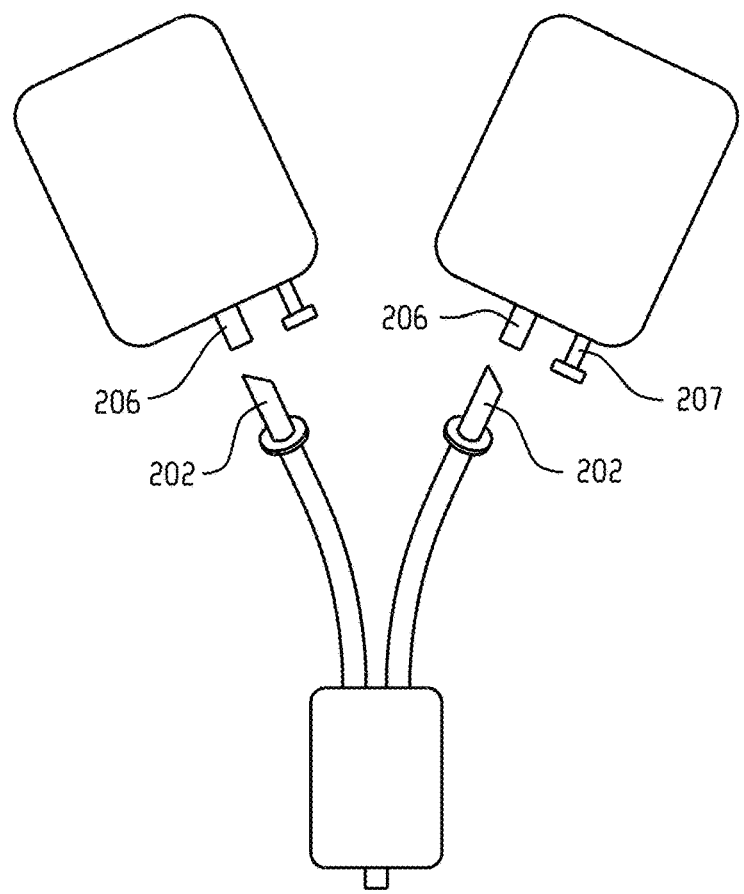
FIG. 12 shows two spikes of a typical "Y-piece" (blood transfusion tubing) coming into contact with an infusion port of an intravenous solution bag (on the left) and a blood or blood product bag (on the right)

FIG. 12 shows two spikes 202 of a typical "Y-piece" (blood transfusion tubing) coming into contact with an infusion port of the intravenous solution bag (left) and blood or blood product bag (right). Both bags have an infusion port 206 where the spike 202 enters and an injection port 207 where the needle penetrates to inject the medication or draw blood or fluid therefrom.

Figure 13A:
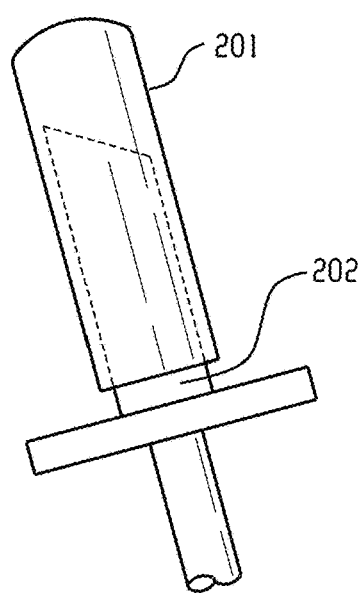
FIG. 13A shows a typical blood transfusion tubing spike covered with the plastic protective cover.

FIG. 13A shows a typical spike 202 covered with a typical, plastic protective cover 201.

Figure 13B:
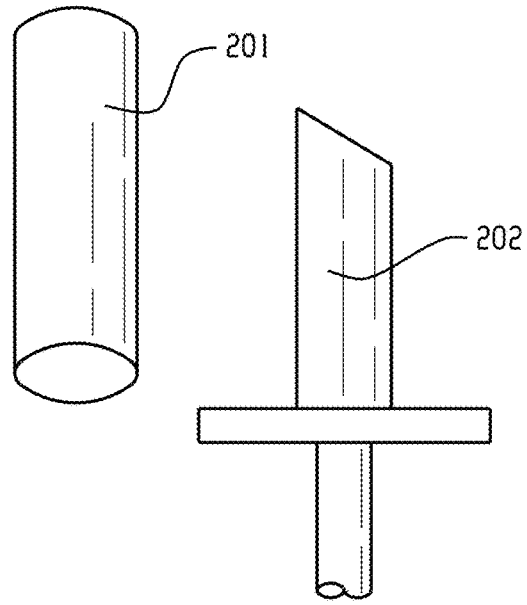
FIG. 13B shows a typical blood transfusion tubing spike with the plastic protective cover removed.

FIG. 13B shows the spike 202 having the cover removed. Before the first use, this cover is removed and may be lost, thrown into a trash can or placed on a contaminated surface. The spike then penetrates the infusion port of the bag and the fluid flow starts from the bag into the patient's circulation. When this first bag is empty, the provider removes the spike from the bag and throws the bag away. Sometimes there is a delay before the same spike is used to penetrate another bag, so the protective cover is used to cover the spike. It is very important that the spike 202 is sterile, otherwise the content of the second bag may become contaminated, and the contaminated fluid may enter the patient's circulation. The infusion port 206 on the bag is well-protected with a protective cover which must be removed prior to the spiking. Thus, the danger usually comes from the contaminated spike. The other port on the bag, which is the injection port 207, has a rubber membrane. It is usually exposed and needs to be wiped with an alcohol swab before the needle enters it.

Figure 14A:
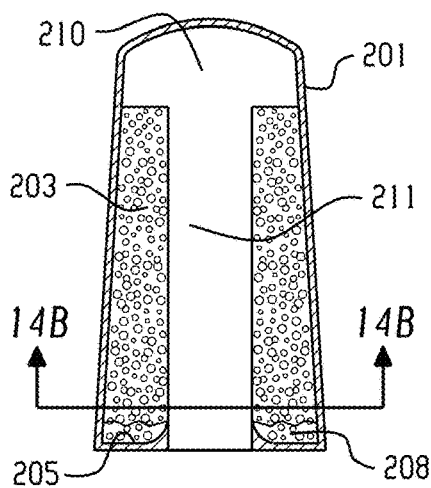
FIG. 14A shows the longitudinal cross-section of the device according to an embodiment, the shape and size of which is equal to a typical spike protective cover.

FIG. 14A shows the disinfecting apparatus containing a plastic cover 201, the shape and size of which corresponds to the shape and size of a typical cover used to cover a spike on a blood transfusion tubing. The plastic cover 201 can be made from the same material as the typical cover or from a different material which provides good fluid barrier. Located inside this cover 201 is a disinfecting pad 203 soaked with the disinfecting agent 208. The disinfecting pad 203 is attached to the wall of the cover 201 to form a chamber 210 and a central lumen 211. Located opposite to the bottom of the device is a receiving member (plate) 205 having an entry for the spike 202 and which comprises the open end of the device. The entry of the plate 205 helps the spike 202 and the device attach to each other by a slip lock mechanism although other mechanisms can be used too. The central part of the plate 205 is slightly elevated in order to minimize the loss of the disinfecting agent 208 during the process of removing the cover 201 from the spike 202.

Figure 14B:
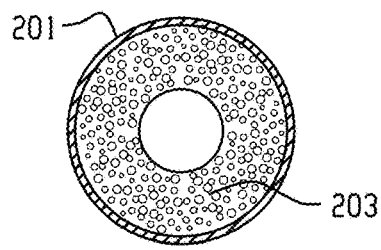
FIG. 14B shows a transverse cross-sectional view of the same device, according to an embodiment.

FIG. 14B shows a transverse cross-sectional view of the same apparatus with the disinfecting pad 203 located inside.

Figure 14C:
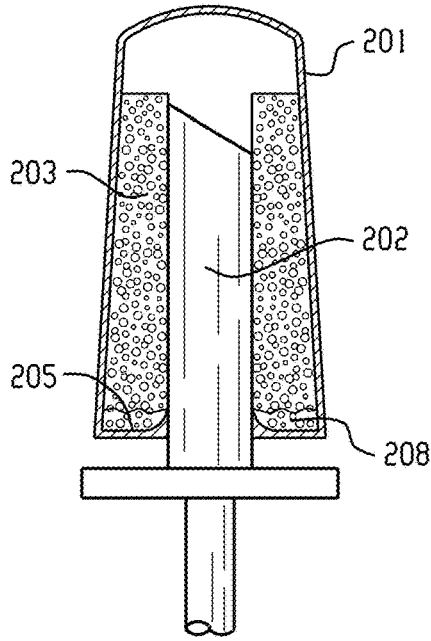
FIG. 14C shows the same device as a longitudinal cross-section according to an embodiment, located at the top of a typical spike.

FIG. 14C shows the same disinfecting apparatus at the top of a typical blood transfusion tubing spike 202. The disinfecting pad 203 contacts and sterilizes the spike 202 to get it ready for the next use. The disinfecting pad 203 lines the interior of the housing (plastic cover) 201 and is affixed to the surface of the cavity. The disinfecting pad 203 does not completely fill out the entire housing 201. It leaves a cavity (a hollow or a central accepting chamber), which matches the size and shape of the typical blood transfusion spike. This compatibility guarantees that the disinfecting pad 203 comes into close contact with the spike 202. In another embodiment, the internal diameter of the lumen may be less than the external diameter of the spike. As the spike is ordinarily not as sharp as a needle, it may enter a narrower lumen without puncturing or penetrating the disinfecting pad. In yet another embodiment, the disinfecting pad may not form a lumen at all, but instead may have, for example, two perpendicular splits that would accept the spike inside the disinfecting apparatus (the diameter of the lumen is about 0) as the portions of the pad comprising the splits are compressed by the medical object such as a medical spike. The disinfecting pad 203 needs to have good absorption capacity. Movement of the device also causes the disinfecting agent 208 to migrate inside the housing (plastic cover) 201 and keeps all areas of the pad 203 soaked. The disinfecting pad 203 can be made from any suitable material having good absorbing ability, for example, a sponge. The disinfecting agent may include an antibacterial agent, an antiviral agent, or a combination thereof.

Figure 15A:
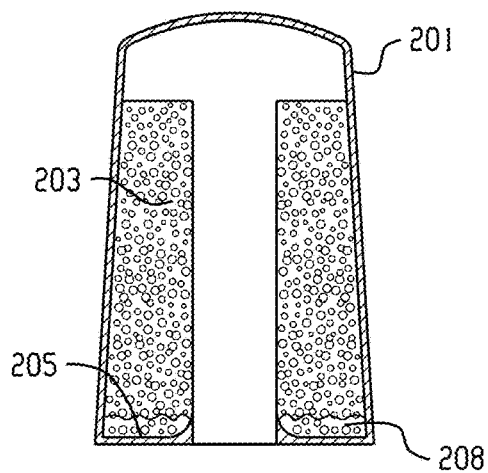
FIG. 15A shows a modified device according to an embodiment, having a larger disinfecting pad.

FIG. 15A shows a slightly different device having an opening on the floor 205 corresponding in size and shape to the size and shape of a typical spike 202. Above this slip locking part is a wider cover 201 which allows a larger disinfecting pad 203 with more disinfecting agent 208 to fit in. The central part of the floor 205 is also elevated to minimize the loss of the disinfecting agent 208.

Figure 15B:
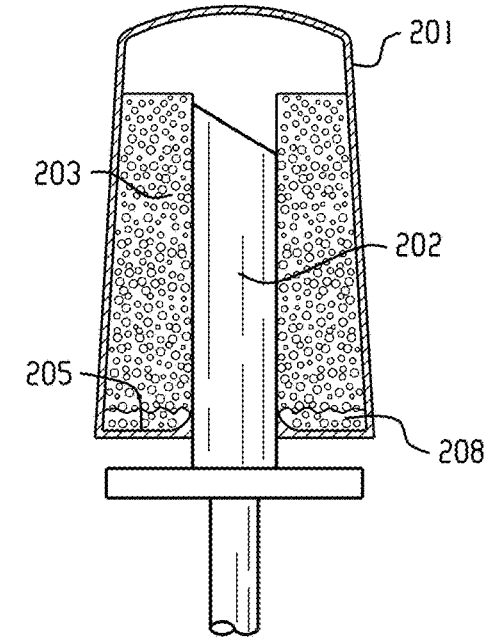
FIG. 15B shows the same device according to an embodiment, which is placed at the top of the spike.

FIG. 15B shows the devices described above when they are placed at the top of a typical blood transfusion spike. The disinfecting pad 203 touches the spike 202 and keeps it sterile until the next use. The plate 205 assists in attaching the spike and prevents the disinfecting agent 208 loss by creating a good seal.

Figure 16A:
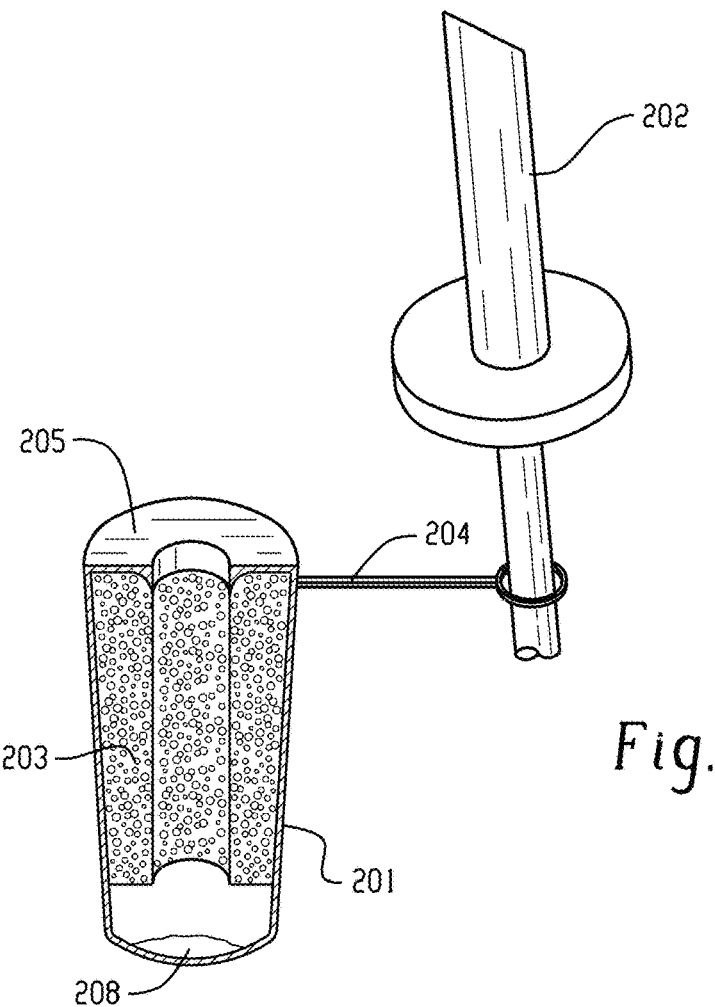
FIG. 16A shows a device as a longitudinal cross-section according to an embodiment, which is removed from the spike but attached to blood transfusion tubing by a band (loop)

FIG. 16A shows a typical blood transfusion tubing with a spike 202 at the top. The same two spikes are present on "Level 1" rapid transfusion tubing too. On the right is the device shown in FIG. 13A, which is attached by the optional (additional) elastic band 204 to the left side of blood transfusion tubing. The band 204 is sufficiently elastic to allow the device to cover the spike 202. It is also sufficiently durable to allow for multiple covering and uncovering of the spike 202. The exact place of the attachment may vary. The band 204 keeps the device close to the spike and reminds the provider to cover the spike 202 after the spike has been removed from the bag. The band also keeps the device inverted and helps prevent spillage and loss of the disinfecting agent which may happen when the device is placed on a surface. The band also prevents the device from being placed on a contaminated surface.

Figure 16B:
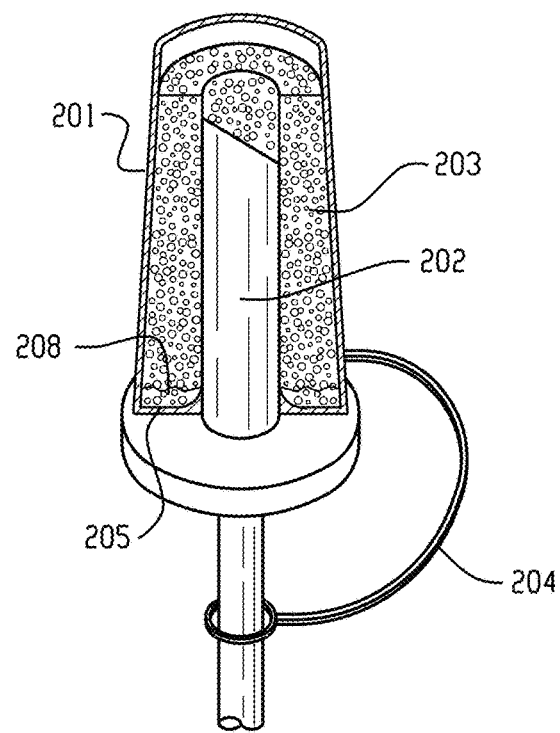
FIG. 16B shows the same device as a longitudinal cross-section according to an embodiment, at the top of the spike.

FIG. 16B shows the device placed at the top of the spike 202. The disinfecting pad 203 contacts and sterilizes the spike 202, while the plate 205 provides a good seal. The device is also shown with an optional band 204 which connects the device with the right side of the tubing. The device is now ready for the next use and spiking of another IV bag.

A typical plastic cover of a typical blood transfusion spike is usually removed the very first time and may be either lost or placed on a contaminated surface. The spike would then be used to spike the bag. After all contents of the bag enter a patient's circulation, the spike would be removed from the bag and the bag would be discarded. The spike which may be stained with blood when it is used to spike a bag with the blood, would then be left hanging in the air, and thus exposed to environmental contamination when the misplaced plastic cover is not applied to cover the spike. The cover may be contaminated, and the contaminated cover may be placed at the top of the spike. This would lead to contamination of the new bag when the contaminated spike enters the bag. It is very common during blood transfusion for the same spike to enter several different bags, and especially when a patient has substantial bleeding, the spike may enter more than ten times. These cases are also associated with a high level of stress where the provider cannot find the cover or does not have time to apply a plastic cover, and where strict sterile techniques are difficult to follow.

It is understood that in addition to the above mentioned disinfecting devices for needles and IV tubing spikes, the same principles can be used to cover and sterilize many other sharp objects used to penetrate different membranes, an IV bag, a tubing, or a patient's body. There are many intravenous or intra-arterial catheters which would benefit from this device in order to prevent blood stream infection. The present inventive concept has been described in terms of exemplary principles and embodiments, but those skilled in the art will recognize that variations may be made and equivalents substituted for what is described without departing from the scope and spirit of the disclosure as defined by the following claims.

The invention claimed is:

1. A disinfecting capping device for a sharp medical object, comprising:
   a container comprising a bottom, an open end opposite to the bottom, and a side disposed between the open end and the bottom of the container, and
   a first disinfecting member disposed on the internal surface of the side of the container between the open end and the bottom thereof so as to form a hollow cavity containing no fluid for receiving the sharp medical object through the open end of the container,
   wherein the cavity extends continuously from the open end of the container to the bottom thereof.

2. The disinfecting capping device of claim 1, wherein the open end of the container comprises a funnel having a proximal end and a distal end so as to guide the sharp medical object through the distal end inside the cavity of the first disinfecting member.

3. The disinfecting capping device of claim 1, wherein a diameter of the cavity is equal to or less than an external diameter of the sharp medical object.

4. The disinfecting capping device of claim 1, wherein the disinfecting capping device further comprises a first chamber formed by the first disinfecting member, the bottom of the container, and optionally, the side of the container, wherein the first chamber is in communication with the cavity of the container.

5. The disinfecting capping device of claim 1, wherein the first disinfecting member is permanently affixed to the internal surface of the side of the container, and optionally, to the bottom thereof.

6. The disinfecting capping device of claim 1, wherein the first disinfecting member is impregnated with a disinfecting agent.

7. The disinfecting capping device of claim 6, wherein the disinfecting agent is an anti-bacterial agent, an anti-viral agent, or a combination thereof.

8. The disinfecting capping device of claim 1, further comprising:
    an external member attached to an external surface of the bottom of the container and comprising an internal surface, and
    a second disinfecting member disposed on the internal surface of the external member.

9. The disinfecting capping device of claim 8, further comprising:
    a cap covering the second disinfecting member.

10. The disinfecting capping device of claim 9, wherein the cap forms a seal with the external member of the container.

11. The disinfecting capping device of claim 8, wherein the external member is permanently affixed to the bottom of the container.

12. The disinfecting capping device of claim 8, wherein the second disinfecting member is attached to the internal surface of the external member.

13. A disinfecting capping device for a sharp medical object, comprising:
    a container comprising a bottom, an open end opposite to the bottom, and a side disposed between the open end and the bottom of the container, and
    a first disinfecting member disposed on the internal surface of the side of the container between the open end and the bottom thereof so as to form a hollow cavity containing no fluid for receiving the sharp medical object through the open end of the container,
    wherein the open end of the container comprises a receiving member so as to guide the sharp medical object inside the cavity of the container, and
    wherein the cavity extends continuously from the open end of the container to the bottom thereof.

14. A method for disinfecting a sharp medical object, comprising:
    providing a disinfecting capping device for a sharp medical object, comprising:
        a container comprising a bottom, an open end opposite to the bottom, and a side disposed between the open end and the bottom of the container, and
        a first disinfecting member disposed on the internal surface of the side of the container between the open end and the bottom thereof so as to form a hollow cavity containing no fluid for receiving the sharp medical object through the open end of the container,
        wherein the cavity extends continuously from the open end of the container to the bottom thereof,
    inserting the sharp medical object through the open end into the container to bring an external surface of the sharp medical object in contact with the first disinfecting member, and
    disinfecting the external surface of the sharp medical object.

15. The method of claim 14, wherein the disinfecting capping device further comprises a first chamber formed by the first disinfecting member, the bottom of the container, and optionally, the side of the container, wherein the first chamber is in communication with the cavity of the container.

16. The method of claim 14, further comprising:
    removing the disinfected sharp medical object from the disinfecting capping device, and
    reusing the sharp medical object.

* * * * *